(12) United States Patent
Rousseau et al.

(10) Patent No.: US 8,905,033 B2
(45) Date of Patent: Dec. 9, 2014

(54) MODULAR TISSUE SECUREMENT SYSTEMS

(75) Inventors: Robert Rousseau, Ottsville, PA (US); David Lindh, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 336 days.

(21) Appl. No.: 13/247,713

(22) Filed: Sep. 28, 2011

(65) Prior Publication Data

US 2013/0074849 A1    Mar. 28, 2013

(51) Int. Cl.
*A61F 5/56* (2006.01)

(52) U.S. Cl.
USPC ............................ 128/848; 606/222; 606/224

(58) Field of Classification Search
USPC .......... 128/848; 606/219, 221, 222, 224, 225, 606/228
See application file for complete search history.

(56) References Cited

U.S. PATENT DOCUMENTS

| | | | |
|---|---|---|---|
| 3,123,077 A | 3/1964 | Alcamo | |
| 3,378,010 A | 4/1968 | Codling et al. | |
| 4,069,825 A | 1/1978 | Akiyama | |
| 4,290,763 A | 9/1981 | Hurst | |
| 4,557,264 A | 12/1985 | Hinsch | |
| 4,839,215 A | 6/1989 | Starling et al. | |
| 4,881,939 A | 11/1989 | Newman | |
| 4,950,285 A | 8/1990 | Wilk | |
| 5,053,047 A | 10/1991 | Yoon | |
| 5,123,913 A | 6/1992 | Wilk et al. | |
| 5,192,271 A * | 3/1993 | Kalb et al. ..................... | 604/116 |
| 5,192,274 A | 3/1993 | Bierman | |
| 5,269,783 A | 12/1993 | Sander | |
| 5,284,161 A | 2/1994 | Karell | |
| 5,311,028 A | 5/1994 | Glavish | |
| 5,393,984 A | 2/1995 | Glavish | |
| 5,483,077 A | 1/1996 | Glavish | |
| 5,484,444 A | 1/1996 | Braunschweiler et al. | |
| 5,609,559 A | 3/1997 | Weitzner | |
| 5,683,417 A | 11/1997 | Cooper | |
| 5,704,895 A | 1/1998 | Scott et al. | |
| 5,792,067 A | 8/1998 | Karell | |
| 5,843,077 A | 12/1998 | Edwards | |
| 5,931,855 A | 8/1999 | Buncke | |
| 6,161,541 A | 12/2000 | Woodson | |
| 6,190,401 B1 * | 2/2001 | Green et al. ................... | 606/224 |
| 6,241,747 B1 | 6/2001 | Ruff | |
| 6,250,307 B1 | 6/2001 | Conrad et al. | |
| 6,348,156 B1 | 2/2002 | Vishnoi et al. | |
| 6,431,174 B1 | 8/2002 | Knudson et al. | |
| 6,432,437 B1 | 8/2002 | Hubbard | |

(Continued)

FOREIGN PATENT DOCUMENTS

| | | |
|---|---|---|
| CN | 2465680 | 12/2001 |
| CN | 201029957 | 3/2008 |

(Continued)

OTHER PUBLICATIONS

U.S. Appl. No. 12/182,402, filed Jul. 30, 2008.

(Continued)

*Primary Examiner* — Michael A. Brown (57) ABSTRACT

A system and method are disclosed for the securement of tissue and in particular for placement of a tongue base suspension fiber for the treatment of obstructive sleep apnea. The system incorporates disposable connectors with releasable needles to facilitate the placement of fibers with minimal increase in suture site dilation or trauma.

11 Claims, 7 Drawing Sheets

(56) References Cited

U.S. PATENT DOCUMENTS

| | | |
|---|---|---|
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 * | 1/2006 | Jamiolkowski et al. ........ 600/30 |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 8,307,831 B2 | 11/2012 | Rousseau |
| 8,413,661 B2 | 4/2013 | Rousseau et al. |
| 2001/0037133 A1 | 11/2001 | Knudson et al. |
| 2002/0144685 A1 | 10/2002 | Ivanovich et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0149488 A1 | 8/2003 | Metzger et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0044366 A1 | 3/2004 | Bonutti et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze et al. |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102004 A1 | 5/2007 | Nelson et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0267027 A1 | 11/2007 | Nelson et al. |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1 | 7/2010 | Tschopp et al. |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |

(56) References Cited

U.S. PATENT DOCUMENTS

| | | | |
|---|---|---|---|
| 2011/0144558 | A1 | 6/2011 | Rousseau |
| 2011/0174315 | A1 | 7/2011 | Zhang et al. |
| 2011/0178439 | A1 | 7/2011 | Irwin et al. |
| 2011/0238111 | A1 | 9/2011 | Frank |
| 2012/0123449 | A1* | 5/2012 | Schaller et al. ............ 606/151 |
| 2012/0245629 | A1 | 9/2012 | Gross et al. |
| 2013/0074849 | A1 | 3/2013 | Rousseau et al. |
| 2013/0098371 | A1 | 4/2013 | Rousseau et al. |
| 2013/0118505 | A1 | 5/2013 | Rousseau et al. |
| 2013/0133669 | A1 | 5/2013 | Rousseau |
| 2013/0150872 | A1 | 6/2013 | Rousseau |
| 2013/0174857 | A1 | 7/2013 | Rousseau et al. |
| 2013/0186412 | A1 | 7/2013 | Weadock et al. |
| 2013/0319427 | A1 | 12/2013 | Sung et al. |

FOREIGN PATENT DOCUMENTS

| | | |
|---|---|---|
| CN | 102198010 | 9/2011 |
| CN | 102271624 | 12/2011 |
| DE | 10245076 | 4/2004 |
| EP | 2145587 | 1/2010 |
| EP | 2386252 | 11/2011 |
| EP | 2517633 | 10/2012 |
| FR | 2651113 | 3/1991 |
| JP | 11-514266 | 12/1999 |
| JP | 2001-145646 | 5/2001 |
| JP | 2003265621 | 9/2003 |
| JP | 2006-517115 | 7/2006 |
| JP | 2007-512090 | 5/2007 |
| RU | 2005447 | 1/1994 |
| RU | 2202313 | 4/2003 |
| SU | 927236 | 5/1982 |
| SU | 1697792 | 12/1991 |
| WO | WO 97/13465 | 4/1997 |
| WO | WO 99/00058 A1 | 1/1999 |
| WO | WO 00/66050 | 11/2000 |
| WO | WO 01/21107 | 3/2001 |
| WO | WO 03/096928 | 11/2003 |
| WO | WO 2004/016196 | 2/2004 |
| WO | WO 2004/021869 | 3/2004 |
| WO | WO 2004/021870 A2 | 3/2004 |
| WO | WO 2004/021870 A3 | 3/2004 |
| WO | WO 2004/060311 A2 | 7/2004 |
| WO | WO 2004/060311 A3 | 7/2004 |
| WO | WO 2004/084709 A2 | 10/2004 |
| WO | WO 2004/084709 A3 | 10/2004 |
| WO | WO 2005/046554 A2 | 5/2005 |
| WO | WO 2005/046554 A3 | 5/2005 |
| WO | WO 2005/051292 A2 | 6/2005 |
| WO | WO 2005/082452 A1 | 9/2005 |
| WO | WO 2005/122954 A1 | 12/2005 |
| WO | WO 2006/012188 A1 | 2/2006 |
| WO | WO 2006/072571 A1 | 7/2006 |
| WO | WO 2006/108145 A1 | 10/2006 |
| WO | WO 2007/056583 A1 | 5/2007 |
| WO | WO 2007/075394 A2 | 7/2007 |
| WO | WO 2007/075394 A3 | 7/2007 |
| WO | WO 2007/132449 A2 | 11/2007 |
| WO | WO 2007/132449 A3 | 11/2007 |
| WO | WO 2007/134005 A1 | 11/2007 |
| WO | WO 2007/146338 A2 | 12/2007 |
| WO | WO 2007/149469 A2 | 12/2007 |
| WO | WO 2007/149469 A3 | 12/2007 |
| WO | WO 2008/118913 | 10/2008 |
| WO | WO 2009/023256 A2 | 2/2009 |
| WO | WO 2009/036094 A2 | 2/2009 |
| WO | WO 2010/065341 A2 | 3/2009 |
| WO | WO 2010/065341 A3 | 3/2009 |
| WO | WO 2010/019376 | 2/2010 |
| WO | WO 2010/035303 | 4/2010 |
| WO | WO 2012/004758 | 1/2012 |
| WO | WO 2012/041205 | 4/2012 |
| WO | WO 2012/064902 | 5/2012 |
| WO | WO 2012/170468 | 12/2012 |

OTHER PUBLICATIONS

U.S. Appl. No. 12/183,955, filed Jul. 31, 2008.
U.S. Appl. No. 12/228,681, filed Aug. 14, 2008.
U.S. Appl. No. 12/238,991, filed Sep. 26, 2008.
U.S. Appl. No. 12/257,563, filed Oct. 24, 2008.
U.S. Appl. No. 12/261,102, filed Oct. 30, 2008.
U.S. Appl. No. 12/325,350, filed Dec. 1, 2008.
U.S. Appl. No. 12/378,573, filed Feb. 17, 2009.
U.S. Appl. No. 12/402,631, filed Mar. 12, 2009.
U.S. Appl. No. 13/247,713, filed Sep. 28, 2011.
U.S. Appl. No. 13/279,384, filed Oct. 24, 2011.
U.S. Appl. No. 13/314,704, filed Dec. 8, 2011.
Notification of Transmittal of the International Search Report and the Written Opinion of the International Search Authority or the Declaration mailed on Feb. 3, 2010; PCT/US2009/051921; International Filing Date: Jul. 28, 2009.
Notification of Transmittal of the International Search Report and the Written Opinion of the International Search Authority or the Declaration mailed on May 25, 2010; PCT/US2010/023152; International Filing Date: Feb. 4, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Dec. 29, 2009 for International Patent Application No. PCT/US2009/061455.
International Search Report dated Jan. 21, 2010 for International Patent Application No. PCT/US2009/052110.
International Search Report dated Apr. 29, 2010 for International Patent Application No. PCT/US2009/065293.
International Search Report dated May 25, 2010 for International Patent Application No. PCT/US2010/023152.
International Search Report dated May 25, 2010 for International Patent Application No. PCT/US2010/025778.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
International Search Report re: PCT/US2012/0565677 dated Nov. 27, 2012.
International Search Report dated Apr. 2, 2013 for International Patent Application No. PCT/US2012/067708.
International Search Report dated Apr. 9, 2013 for International Patent Application No. PCT/US2012/061569.
International Search Report dated May 24, 2013 for International Patent Application No. PCT/US2012/066011.
International Search Report dated Oct. 2, 2013 re: PCT/US2013/043238.
Database WPI Week 198312, Thomson Scientific, London, GB; AN 1983-D9513K XP002693421, -& SU 927 236 A1 (Petrozazodsk Univ) May 15, 1982 abstract (see figures 7 & 8).
Friedman et al., "A System and Method for Inserting a Medical Device for Treatment of Sleep Apnea via the Nasal Passage, and Device Therefor", Dec. 29, 2008, U.S. Appl. No. 61/203,758, p. 8 & p. 6/8.
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm.
Cole et al., "Snoring: A Review and a Reassessment", J. of Otolaryngology, vol. 24, No. 5 pp. 303-306 (1995).
Harries et al., "The Surgical treatment of snoring", J. of Laryngology and Otology, vol. 110, Issue 12 pp. 1105-1106 (1996).
Huang et al., "Biomechanics of snoring", Endeavour, vol. 19(3): pp. 96-100 (1995).

(56) References Cited

OTHER PUBLICATIONS

Pang, Kenny et al., "Tongue Suspension Suture in Obstructive Sleep Apnea", Operative Techniques in Otolaryngology, vol. 17, No. 4, pp. 252-256 (2006).

Repose Genioglossus Advancement, Influent Medical, www.influent.com, 1 page (2008).

Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).

Schwab et al., "Upper airway and soft tissue changes induced by CPAP in normal subject", Am. J. Respit. Crit. Care Med., vol. 154, No. 4 pp. 1106-1116 (1996).

Schwartz et al., "Effects of electrical stimulation to the soft palate on snoring and obstructive sleep apnea", J. Prosthetic Dentistry, vol. 76 pp. 273-281 (1996).

Shamsuzzaman et al., "Obstructive Sleep Apnea; Implications for Cardiac and Vascular Disease", JAMA vol. 290, No. 14 pp. 1906-1914 (2003).

Teles et al., "Use of Palatal Lift Prosthesis on Patient Submitted to Maxillectomy: A Case Report", Applied Cancer Res. vol. 25(3), pp. 151-154 (2005).

The Advance System, Aspire Medical, Inc. www.aspiremedical.com, 3 pp (2008).

The Pillar Procedure, Restore Medical, Inc. www.restoremedical.com, 2 pp (2008).

Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 116 pp. 1223-1227 (2006).

Wassmuth et al., "Cautery-assisted palatal stiffening operation for the treatment of obstructive sleep apnea syndrome", Otolaryngology—Head and Neck Surgery, vol. 123, pp. 55-60 (2000).

Wiltfang et al., "First results on daytime submandibular electrostimulation of suprahyoidal muscles to prevent night-time hypopharyngeal collapse in obstructive sleep apnea syndrome", Intl J. of Oral & Maxillofacial Surgery vol. 28 pp. 21-25 (1999).

* cited by examiner

MODULAR TISSUE SECUREMENT SYSTEMS

BACKGROUND OF THE INVENTION

1. Field of the Invention

This invention generally relates to systems to secure tissue, more particularly to tissue securement systems for treatment of obstructive sleep apnea.

2. Related Art

Obstructive sleep apnea (OSA) is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and motor vehicle crashes. Despite the seriousness of OSA, a general lack of awareness among the public and healthcare professionals results in the vast majority of OSA sufferers remaining undiagnosed and untreated.

In the human body, an air filled space between the nasal cavity and the larynx is referred to as the upper airway. The most critical part of the upper airway associated with sleep disorders is the pharynx. The pharynx has three different anatomical levels. The nasopharynx is the upper portion of the pharynx located in the back of the nasal cavity. The oropharynx is the intermediate portion of the pharynx containing the soft palate, the epiglottis, and the curve at the back of the tongue. The hypopharynx is the lower portion of the pharynx located below the soft tissue of the oropharynx. The oropharynx is the section of the pharynx that is most likely to collapse due to the high prevalence of soft tissue structure, which leaves less space for airflow. The hypopharynx lies below the aperture of the larynx and behind the larynx, and extends to the esophagus.

As is well known to those skilled in the art, the soft palate and the tongue are both flexible structures. The soft palate provides a barrier between the nasal cavity and the mouth. In many instances, the soft palate is longer than necessary and it extends a significant distance between the back of the tongue and the posterior pharyngeal wall.

Although the muscles relax throughout the body during sleep, most of the muscles of the respiratory system remain active. During inhalation, the diaphragm contracts and causes negative pressure to draw air into the nasal cavity and the mouth. The air then flows past the pharynx, through the trachea and into the lungs. The negative pressure causes the tissue of the upper airway to deform slightly, which narrows the airway passage. In apneic patients, the soft palate, the tongue, and/or the epiglottis collapse against the posterior pharyngeal wall to block airflow into the trachea. As the airway narrows, airflow through the pharynx becomes turbulent which causes the soft palate to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

When an individual is awake, the back of the tongue and the soft palate maintain their shape and tone due to their respective internal muscles. As a result, the airway through the pharynx remains open and unobstructed. During sleep, however, the muscle tone decreases and the posterior surface of the tongue and the soft palate become more flexible and distensible. Without normal muscle tone to keep their shape and to keep them in place either alone or as a group, the posterior surface of the tongue, the epiglottis, and the soft palate tend to easily collapse to block the airway.

U.S. Pat. No. 7,367,340 describes one approach to treat sleep apnea and is directed to the use of an element that is anchored to the mandible and is capable of applying force within the tongue to prevent the tongue from collapsing during sleep. In the embodiments described, the device consists of an element that is attached to the mandible though drilling of the mandible to provide a rigid point of fixation. The method of attachment risks damaging the dental anatomy and nerve structures within the mandible.

A commercial implant system, sold under the trademark REPOSE™ by InfluENT of Concord, N.H., uses a titanium screw that is inserted into the posterior aspect of the mandible at the floor of the mouth. A loop of suture is passed through the tongue base and attached to the mandibular bone screw. The REPOSE™ procedure achieves a suspension or hammock of the tongue base making it less likely for the base of the tongue to prolapse during sleep. Due to the high activity of the tongue during wakefulness, however, the suture component of this device may act as a cutting element within the tongue, causing device trans-location and ultimately a loss of efficacy of the procedure thereby requiring subsequent removal. Additionally, the fiber is placed within the tongue through the combination of a sterile and non-sterile approach. An incision is made within the sub-mental space to provide access to the infra-mandibular region to place the screw. Once the screw is attached to the mandible, the fiber element is passed into the tongue through the sub-mental musculature, through the genioglossus and exits out of the mucosal surface of the tongue into the contaminated oral cavity. This passage is accomplished through the use of a linear designed suture passer that grasps the fiber, through the use of a jaw like element, and forces it through the tongue in a straight path. Upon exiting in the oral cavity, the fiber is then passed laterally in a sub mucosal pass through the original puncture formed by the curved suture passer which is essentially an eyed needle.

The use of the eyed needle results in the folding of the fiber in half about the eyelet of the needle, thereby increasing, in an irregular fashion, the projected diameter/dissecting cross section of the device. This increase in projected dissection surfaces results in the creation of a larger hole than is necessary for the single strand of fiber that is to be deposited within the tissue tract.

Furthermore, the use of the jawed type linear suture passer also results in an increased projected cross sectional dissecting surface. The fiber is laid into the jaw and is clamped. In the best case scenario, the jaw resultant projected dissecting tissue surface consists of the cross sectional area of the fiber lying alongside the cross sectional area of the shaft of the linear suture passer.

Another commercially available tongue suspension device, developed by ASPIRE Medical, is named the ADVANCE System. It's similar to the REPOSE suture suspension system for the tongue base in that it utilizes a bone screw in the mandible, but has the advantage of being adjustable. The device utilizes a flexible shape memory anchor within the tongue that is shaped similar to a grappling hook to engage the tissue within the tongue base. It's placed through a small incision in the sub-mental region and the suture is attached to a spool-like component attached to the mandible. Two to four weeks after healing, a small incision is made under the chin and a screw is turned to tighten the suture, thus pulling the device forward. While the device provides a simplified installation technique from within the sterile space, the anchors may suffer from a high rate of device fracture and failure due to loading within the tongue musculature. Additionally, the risk of damage to the teeth or the nerve roots for the teeth is similar to the RESPOSE bone screw.

In spite of the above advances in tongue suspension devices, there remains a need for a tongue suspension method and suture passer device that enables the passage of fiber with minimal increase in the size of the dissected tunnel formed in the traverse of the fiber.

SUMMARY OF THE INVENTION

The present invention relates generally to a system for the securement of tissue comprising:

a) a securement fiber comprising a distal end and a proximal end, the distal end further comprising a distal connector and the proximal end further comprising a proximal connector;
b) a needle comprising a proximal end and a distal end, the distal end further comprising a tissue piercing surface and the proximal end comprising a connector, the connector being releasably engageable with the distal connector of the fiber; and
c) a tissue passer comprising a proximal end and a distal end, the distal end releasably engageable with the distal and proximal connectors of the fiber.

This invention also generally relates to tissue securement methods comprising the steps of:

a) piercing the tissue at a first puncture point with a needle having proximal and distal ends that is attached to a securement fiber, the fiber having a first end and a second end with the attachment of the needle to the fiber occurring at the first end of the fiber and the proximal end of the needle;
b) exiting the tissue at a second puncture point with the needle and securement fiber;
c) releasing the needle from the securement fiber while ensuring that the first and second ends of the fiber remain outside of the tissue at the first and second puncture points;
d) passing a fiber passer from a first entry point through the tissue and out of the tissue at the first puncture point;
e) attaching the distal tip of the fiber passer with the second end of the fiber outside of the tissue at the first puncture point;
f) drawing the fiber attached to the fiber passer through the tissue at the first puncture point by pulling the fiber passer with attached fiber through and out of the first entry point;
g) releasing the fiber from the fiber passer;
h) passing the fiber passer from a second entry point through the tissue and out of the tissue at the second puncture point;
i) attaching the distal tip of the fiber passer with the first end of the fiber outside of the tissue at the second puncture point;
j) drawing the fiber attached to the fiber passer through the tissue at the second puncture point by pulling the fiber passer with attached fiber through and out of the second entry point; and
k) releasing the fiber from the fiber passer; and
l) attaching the fiber ends at the first and second entry points to at least one anchor or tying the fiber ends together.

In preferred embodiments, the systems and methods of this invention relate to securement of the tongue.

The systems and methods of this invention provide at least the following advantages. The connector features on the fiber ends enable the use of releasable needles, eliminates the need to thread the suture through a snaring/eyed needle type arrangement, and minimizes the tissue tract diameter for the later passing of the fiber through tissue. The hook type element on the suture passer allows passes through tissue minimizing the dragging or traumatizing of tissue, permits quick connection to connector features on the fibers ends, and in combination with connector features on the fiber, minimizes the diameter of the tissue tract by ensuring trailing arrangement of the fiber without having the fiber being folded over. The releasable needle enables easy attachment/detachment from the fiber and ensures that the trailing arrangement of the fiber without folding over the fiber to minimize the diameter of the fiber tract through the tissue.

DETAILED DESCRIPTION OF PREFERRED EMBODIMENTS OF THE INVENTION

The present invention relates to a tissue securement system that is able to be placed with minimal tissue trauma. The system consists of three key functional components. The system includes a suspension fiber that has modified ends, a releasable needle, and a linear suture passer. The releasable needle and linear suture passer are designed to engage with the modified ends of the suspension fiber.

As used herein, the terms "suture" and "fiber" may be used interchangeably. Additionally, the terms "suture passer", "fiber passer" and "tissue passer" are intended to be used interchangeably.

Figure 1A:
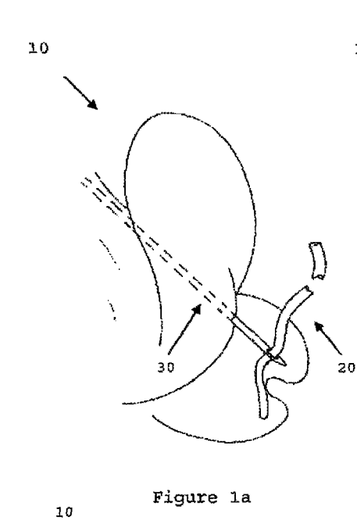
FIGS. 1a-c depict elements of one method of a tissue securement system particularly directed toward the threading of fiber through an eyelet of a linear suture passer and the subsequent passing of the threaded fiber through tissue.
Figure 1B:
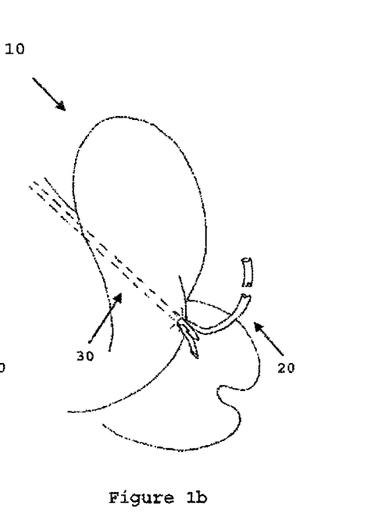
Figure 1C:
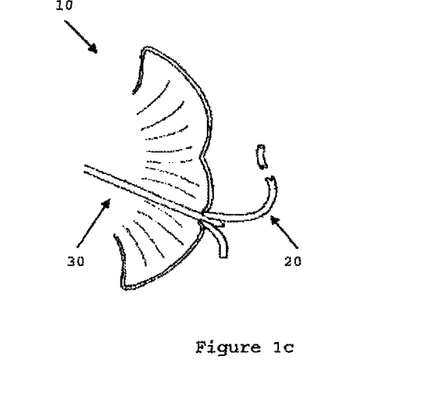

FIGS. 1a-1c illustrate a suspension system for securement of tissue 10 (in this case a tongue) that consists of unmodified fiber 20 and suture passer 30. The suture passer 30 illustrated comprises a tapered tip rod with an eyelet. In use, fiber 20 is manually threaded through the eyelet of suture passer 30 within the oral cavity as shown in FIG. 1a. FIG. 1b depicts fiber 20 as it begins to be drawn by suture passer 30 through tissue 10. FIG. 1c is a cross sectional view of FIG. 1b and shows an alternate view of the path that fiber 20 will take as suture passer 30 is drawn through tissue 10. It can be appreciated that within the limited volume of the oral cavity, that the threading of the fiber requires dexterity and patience since the motion of the suture passer is limited. Additionally, it can be seen that the fiber is folded in half about the eyelet thereby increasing the total cross sectional area of the device as it is pulled into the tissue which is a cause for additional trauma as the doubled over fiber is pulled through the tissue.

Figure 2:
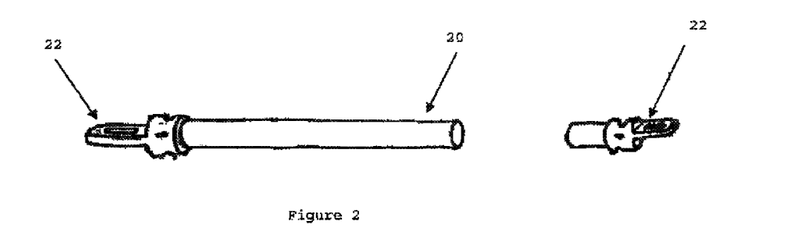
FIG. 2 depicts one embodiment of a fiber component of the present invention with eyeleted connectors attached to the ends of the fiber.

FIG. 2 illustrates an embodiment of fiber component 20 of the tissue securement system with eyeleted connectors 22 attached. Connectors 22 may be attached to fiber 20 by any conventional way including, but not limited to, crimping the connector to the fiber or by applying an adhesive to the connector and/or the fiber. While eyeleted connectors 22 are shown, one skilled in the art would appreciate that alternative connectors may be used that involve geometries that engage with the releasable needle and suture passer. Non-limiting examples of alternative connectors include conical barbs, flat barbs, male detents, hook-like features, magnetic, or magnetic combined with alignment features such as conical ends and receptor geometries.

While the connectors 22 may be added as separate elements affixed to the ends of the fiber as described above, it would be appreciated by those of skill in the art that connectors 22 may be created at the ends of the fiber directly through any number of means, including but not limited to: i) forming eyelets at the ends of the fiber by bending back an end of the fiber and knotting the fiber end with the fiber to form an eyelet, or, in the case of a multifilament fiber, bending back an end of a multifilament fiber and then splicing the end into and among the filaments of the fiber at a distance sufficient from the end of the fiber to form an eyelet; ii) reshaping the fiber ends through mechanical means such as machining, cutting, bending, etc. or iii) shaping the fiber ends into appropriate geometries through the use of energy based forming such as RF tipping, thermal compression molding, ultrasonic forming and other such methods. For example, in the case of thermoplastic resin based fibers, it may desirable to form the tip of the fiber into a conical barb form or eyelet form for engagement with the suture passer. The free end of the fiber is placed within a forming die cavity that is shaped to the final desired geometry. As pressure is applied to the fiber, the thermoplastic resin exceeds the melting point of the material and is reshaped to the final cavity form. The fiber is subsequently removed from the form after sufficient time has occurred for cooling of the fiber material below its melting point. In the case of thermoset resins, or other non-formable materials, the fiber may be produced as an oversized form. The fiber may then be placed into stamping die that is capable of punching out the final form of the fiber with the associated connector end geometry.

Examples of suitable materials for fiber 20 component useful with this invention are any non-absorbable biocompatible suture material. Suitable non-absorbable materials for use in the present invention include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) Poly(hexafluoropropylene-VDF), polyaryletherketones, polyolefins (e.g. polypropylene including isotactic and syndiotactic polypropylene and blends thereof, as well as, blends composed predominately of isotactic or syndiotactic polypropylene blended with heterotactic polypropylene and/or polyethylene (such as is described in U.S. Pat. No. 4,557,264 issued Dec. 10, 1985, assigned to Ethicon, Inc., hereby incorporated by reference in its entirety) and combinations thereof.

In the event that a temporary suspension is desirable, such as in the case of trauma, or radical surgical interventions that may cause swelling of the tongue and associated tissues, or in other locations such as urethra suspension, absorbable fibers may be desirable to provide temporary support until edema/swelling has been reduced. Suitable absorbable materials for use as filaments and/or yarns include, but are not limited to, aliphatic polyesters which include but are not limited to homopolymers and copolymers of lactide (which includes lactic acid d-,l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

Figure 3A:
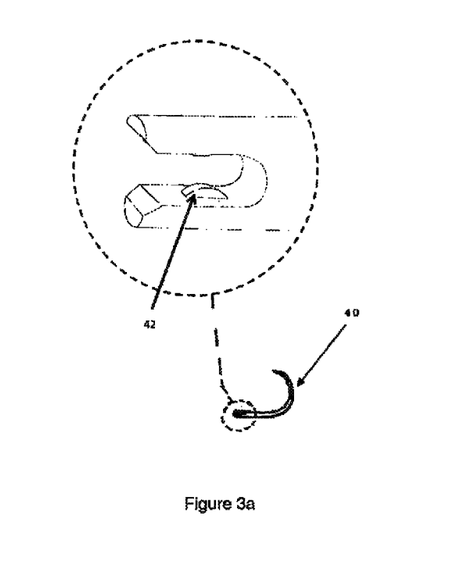
FIGS. 3a-3b show embodiments for a releasably connectible needle and suture passer suitable for use with the system of the present invention.
Figure 3B:
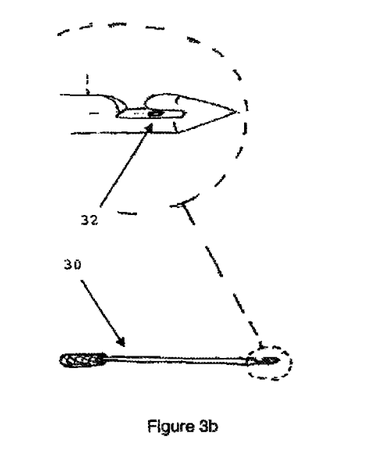

FIGS. 3a and 3b show preferred embodiments in which curved needle 40 and linear suture passer 30 are releasably engageable with fiber 20 having eyelet connectors 22. More specifically, FIG. 3a depicts the overall shape of curved needle 40 with an enlarged view of needle 40's proximal end, which in this embodiment is shown to comprise a recessed area with a detent 42 for releasable engagement with eyelet connectors. Similarly, as depicted in FIG. 3b, suture passer 30 is shown with an enlarged view of its distal tip. Suture passer 30's distal tip comprises a tissue piercing point and a recessed portion comprising a detent 32. When used with fiber 20 having eyelet connectors 22, the detent 32 of suture passer 30 will releasably engage connectors 22 and therefore be capable of drawing fiber 20 through tissue.

Non-limiting examples of suture passer tip designs that may be utilized with the previously disclosed fiber connector ends include conical barbs, flat barbs for joining with fibers having eyeleted ends, female detent pockets, eyelets, hook-like features, quick connect type sleeve arrangements, vacuum wells/surfaces, jaw features, passive magnetic tips, energy based magnetic tips, or magnetic combined with alignment features such as conical ends and receptor geometries.

In use, the system of this invention is capable of securing various types of tissue while minimizing trauma to the tissue compared with tissue securement systems of the prior art.

The tissue securement method using the system of this invention is illustrated in the following figures. While the following method is described for securement of a tongue in a tongue suspension procedure, it should be appreciated by one of skill in the art that the method described is equally applicable to securement or suspension of other types of tissue.

Figure 4:
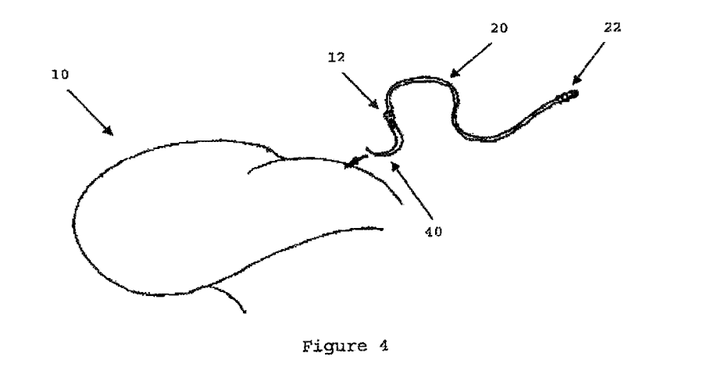
FIG. 4 depicts a releasably engaged needle and fiber approaching tissue to be treated.

Referring to FIG. 4, the tongue suspension procedure is initiated by targeting an area of the tongue to be treated. In this case, lateral passage of the suspension fiber is targeted through the tongue at a location approximately aligned with the median sulcus/circumvallate papillae and is projected to pass through the mucosal surface of the tongue through the use of the releasable needle 40. FIG. 4 illustrates an approach to this surface of the tongue. Specifically, releasable needle 40 engaged with fiber 20 by connector 22, approaches tongue 10.

Figure 5:
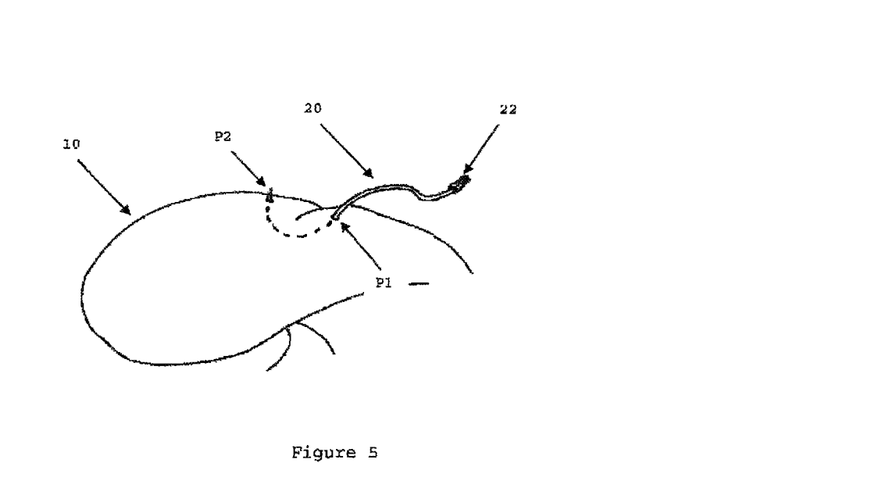
FIG. 5 shows the releasably engaged needle and fiber penetrating and exiting tissue.

FIG. 5 shows the path of needle 40 through tongue 10. Needle 40 creates two punctures ($P_1$ and $P_2$) by entering tongue 10 approximately 1 cm lateral to the midline position ($P_1$) and exiting approximately 1 cm lateral on the opposite side of the midline position ($P_2$). In this embodiment, the proximal connector 22 of fiber 20 is not pulled through and remains outside of tongue 10.

Figure 6:
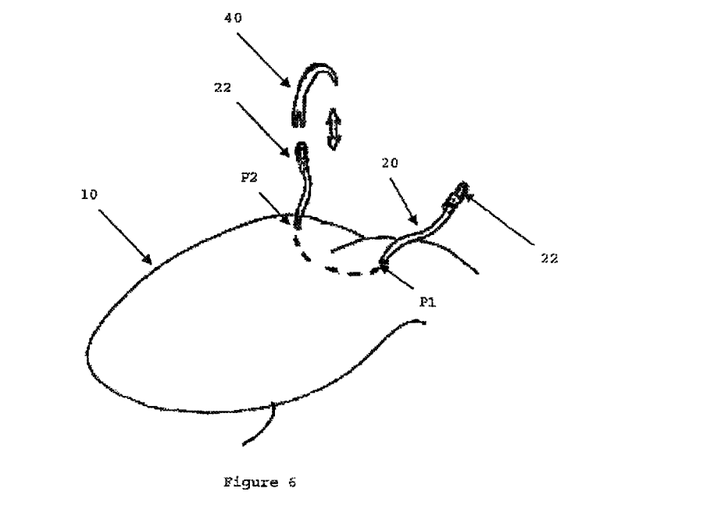
FIG. 6 depicts the releasably engaged needle of FIG. 5 after being released from a securement fiber.

FIG. 6 depicts release of needle 40 from fiber connector 22. Once released, fiber 20 is now ready for further steps to secure submucosal tissue of tongue 10 with proximal and distal connectors 22.

Figure 7:
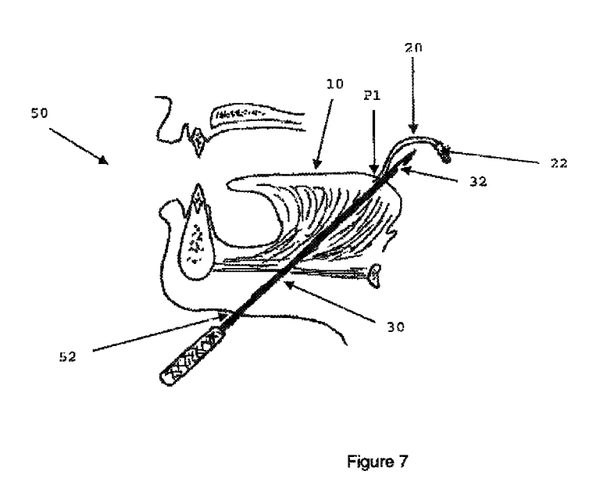
FIG. 7 illustrates use of a fiber passer deployed through the musculature of the tongue to engage connector end of securement fiber.
Figure 8:
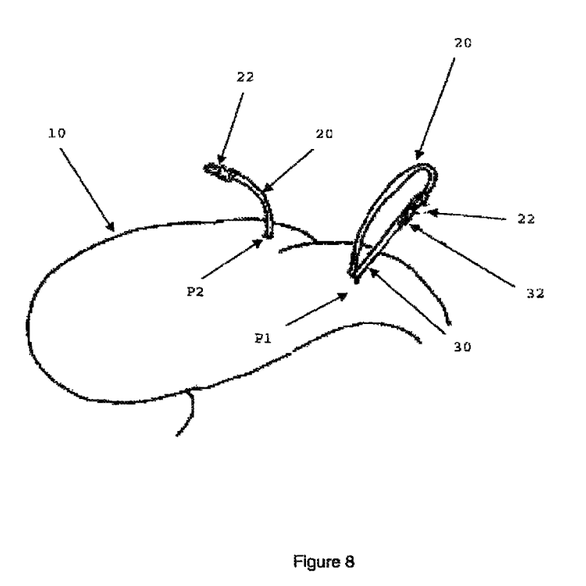
FIG. 8 shows engagement of a fiber passer with a connector at one of the ends of securement fiber prior to pulling of the engaged fiber though tissue.

FIG. 7 shows a cross sectional view of a portion of human head 50 and a further step in practicing the method of this invention. More specifically, fiber passer 30 is passed from within submental incision 52 through the mylohyoid and genioglossus of tongue 10 to an exit point located within the same puncture $P_1$ created by one of the ends of fiber 20. Referring now to FIG. 8, one of the connector ends 22 of fiber 20 is engaged with the engagement element 32 on the end of the fiber passer 30. In this embodiment, engagement element 32 is in the form of a hooked recess at the tip of fiber passer 30. Once element 32 is engaged with fiber 20, the fiber passer 30 is withdrawn to pull the free end of suspension fiber 20 into puncture $P_1$ of tongue 10, through the tongue's musculature and out of submental incision 52. This step is repeated for the second end of the fiber 20 through puncture $P_2$. It is important to note that the free ends of the suspension fiber 20 may be pulled directly through an anchoring element, either rigid or non-rigid, located in the submental dissection 52 or alternatively they may threaded through the anchor after disengagement with fiber passer 30.

Figure 9:
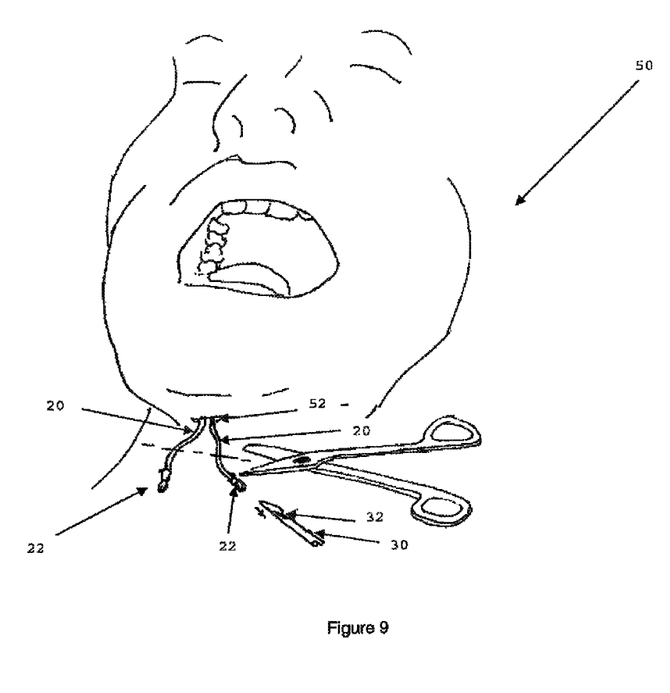
FIG. 9 depicts cutting away of the connectors on the securement fiber ends.

Subsequently, once both ends of fiber 20 are pulled through the musculature and out of submental incision 52, the connector ends 22 are cut off or removed as depicted in FIG. 9.

Once the connectors 22 have been removed, tension is applied to the free ends of fiber 20 to apply the appropriate suspension of the tongue. The free ends of fiber 20 may either be tied to themselves, tied to at least one anchor or may be engaged with a clamping/clipping structure. Common anchoring points for the free ends of fiber 20 include but are not limited to bone or soft tissue. In the case of tongue suspensions, anchoring to the mandible bone such done in the REPOSE and ADVANCE anchoring systems are contemplated. Also anchoring at least one end of the fiber to mesh implanted in soft tissue is contemplated.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A method of securing tissue comprising the steps of:
   a) piercing the tissue at a first puncture point with a needle having proximal and distal ends is attached to a securement fiber, the fiber having a first end and a second end with the attachment of the needle to the fiber occurring at the first end of the fiber and the proximal end of the needle;
   b) exiting the tissue at a second puncture point with the needle and securement fiber;
   c) releasing the needle from the securement fiber while ensuring the first and second ends of the fiber remain outside of the tissue at the first and second puncture points;
   d) passing a fiber passer from a first entry point through the tissue and out of the tissue at the first puncture point;
   e) attaching the distal tip of the fiber passer with the second end of the fiber outside of the tissue at the first puncture point;
   f) drawing the fiber attached to the fiber passer through the tissue at the first puncture point by pulling the fiber passer with attached fiber through and out of the first entry point;
   g) releasing the fiber from the fiber passer;
   h) passing the fiber passer from a second entry point through the tissue and out of the tissue at the second puncture point;
   i) attaching the distal tip of the fiber passer with the first end of the fiber outside of the tissue at the second puncture point;
   j) drawing the fiber attached to the fiber passer through the tissue at the second puncture point by pulling the fiber passer with attached fiber through and out of the second entry point; and
   k) releasing the fiber from the fiber passer; and
   l) attaching the fiber ends at the first and second entry points to at least one anchor or tying the fiber ends together.

2. The method claim 1, wherein the first and second ends of the fiber comprise releasably engageable connectors.

3. The method of claim 2, wherein the connectors are selected from the group consisting of consisting of an eyelet, a barb, a hook and a male detent.

4. The method of claim 3, wherein the connector is an eyelet.

5. The method of claim 4, wherein the distal end of the fiber passer and the proximal end of the needle comprise releasably engagable detents.

6. The method of claim 4, wherein the distal end of the fiber passer comprises a barb.

7. The method of claim 4, wherein the distal end of the fiber passer comprises a hook.

8. The method of claim 1, wherein the tissue is a tongue.

9. The method of claim 8, wherein the first and second puncture points occur on either side of the midline of the tongue.

10. The method of claim 9, wherein the first entry point of the fiber passer occurs at a submental incision at a first location and through the mylohoid and genioglossus of the tongue and out of the first puncture point.

11. The method of claim 9, wherein the second entry point of the fiber passer occurs at the submental incision at a second location and through the mylohoid and genioglossus of the tongue and out of the second puncture point.

* * * * *